United States Patent
Powell

(10) Patent No.: US 10,188,544 B2
(45) Date of Patent: Jan. 29, 2019

(54) PENILE IMPLANT

(71) Applicant: Charles Powell, Torrance, CA (US)

(72) Inventor: Charles Powell, Torrance, CA (US)

(73) Assignee: POWELL DEVELOPMENT GROUP, INC., Carson City, NV (US)

( * ) Notice: Subject to any disclaimer, the term of this patent is extended or adjusted under 35 U.S.C. 154(b) by 320 days.

(21) Appl. No.: 15/053,923

(22) Filed: Feb. 25, 2016

(65) Prior Publication Data

US 2016/0242952 A1    Aug. 25, 2016

Related U.S. Application Data

(60) Provisional application No. 62/120,506, filed on Feb. 25, 2015, provisional application No. 62/172,908, filed on Jun. 9, 2015.

(51) Int. Cl.
| | |
|---|---|
| *A61F 6/04* | (2006.01) |
| *A61F 5/453* | (2006.01) |
| *A61F 5/443* | (2006.01) |
| *A61M 39/08* | (2006.01) |

(52) U.S. Cl.
CPC ............... *A61F 6/04* (2013.01); *A61F 5/443* (2013.01); *A61F 5/453* (2013.01); *A61F 2006/047* (2013.01); *A61M 39/08* (2013.01)

(58) Field of Classification Search
CPC .. A61F 6/04; A61F 5/443; A61F 5/453; A61F 2006/047; A61F 6/065; A61F 5/41; A61F 2006/042; A61F 6/02; A61M 39/08
See application file for complete search history.

(56) References Cited

U.S. PATENT DOCUMENTS

| | | | |
|---|---|---|---|
| 3,677,225 A * | 7/1972 | Czirely | A61F 6/04 |
| | | | 128/844 |
| 4,320,752 A | 3/1982 | Comparetto | |
| 4,769,020 A | 9/1988 | Eaton | |
| 4,821,742 A | 4/1989 | Phelps | |
| 5,458,114 A | 10/1995 | Herr | |
| 5,469,863 A * | 11/1995 | Shah | A41D 19/0068 |
| | | | 128/844 |
| 6,089,231 A * | 7/2000 | Thompson | A61F 6/005 |
| | | | 128/842 |
| 6,148,819 A | 11/2000 | Winkler | |
| 6,491,035 B2 | 12/2002 | Winkler | |
| 6,699,226 B2 | 3/2004 | Velazquez | |
| 8,857,437 B2 | 10/2014 | Powell | |
| 2011/0230851 A1 | 9/2011 | Kay | |
| 2014/0076329 A1 | 3/2014 | Rhodes | |

* cited by examiner

*Primary Examiner* — Ophelia A Hawthorne
(74) *Attorney, Agent, or Firm* — Risso I.P.

(57) ABSTRACT

Described is a penile implement that can be implemented as both a catheter device and a prophylactic device. The penile implement is formed of a top polyurethane film, with a bottom polyurethane film that is RF welded to the top film such that a reservoir exists between the films. An adhesive layer formed on the bottom film and a bottom release layer covers the adhesive layer. Further, a hole is formed in the bottom film. Thus, during use, a user may remove the bottom release layer and adhere the bottom film with a user's penis such that bodily fluids secreted from the user's penis pass through the hole and into the reservoir formed between the top film and bottom film.

18 Claims, 15 Drawing Sheets

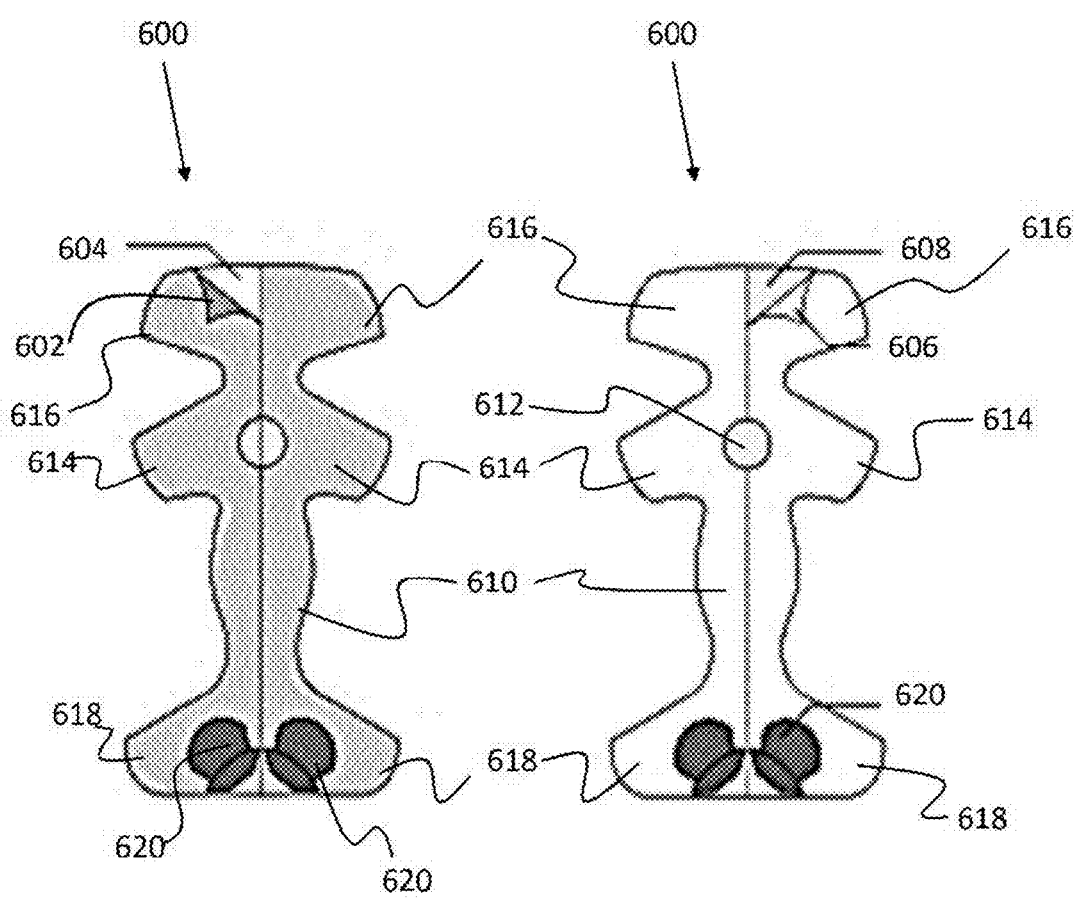

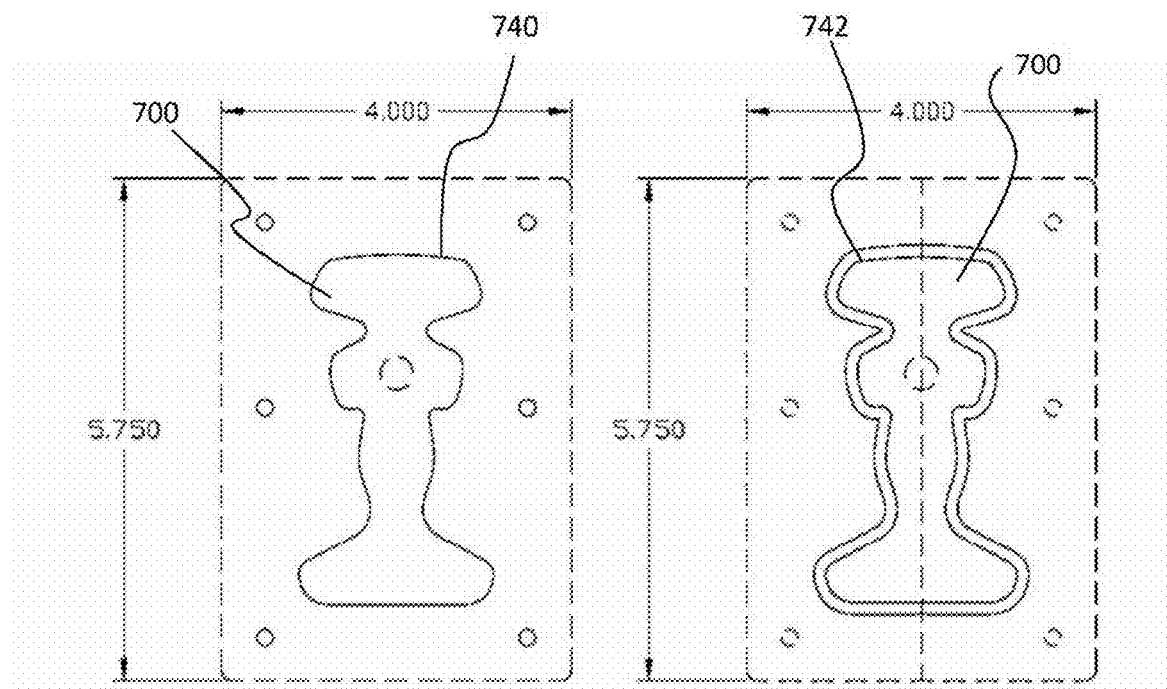

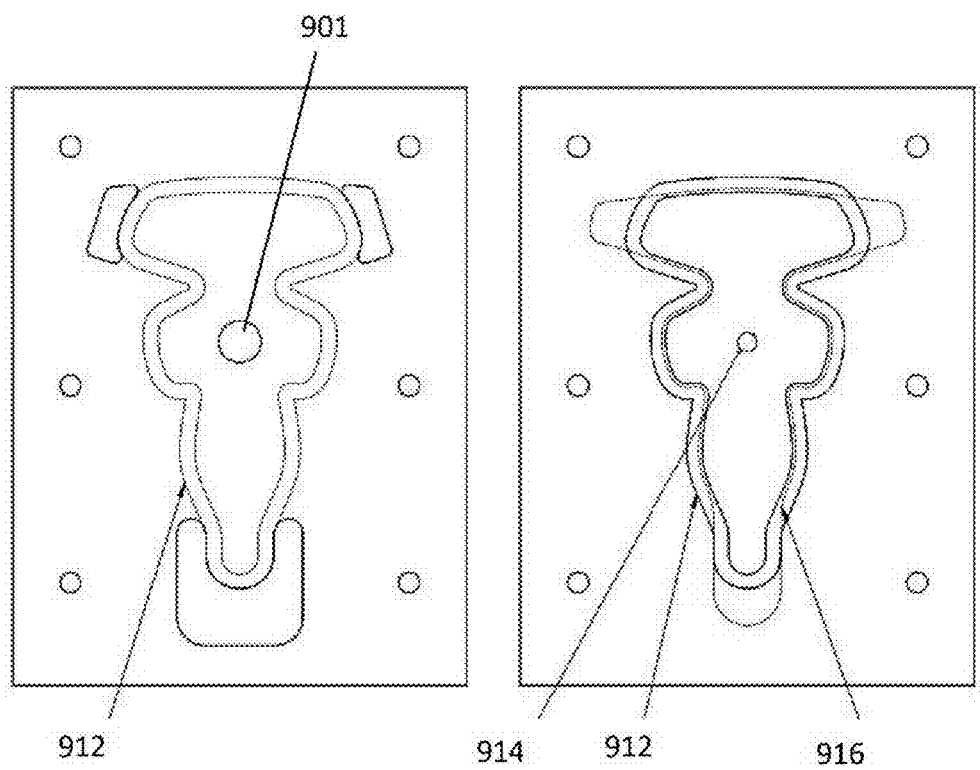

PENILE IMPLANT

CROSS-REFERENCE TO RELATED APPLICATIONS

This is a non-provisional application of U.S. Provisional Application No. 62/120,506, filed on Feb. 25, 2015, the entirety of which is incorporated herein by reference.

This is ALSO a non-provisional application of U.S. Provisional Application No. 62/172,908, filed on Jun. 9, 2015, the entirety of which is incorporated herein by reference.

BACKGROUND OF THE INVENTION (1) Field of Invention

The present invention relates to a penile implement and, more particularly, to a prophylactic device for adhering to the glans of a penis and capturing bodily fluids.

(2) Description of Related Art

Prophylactic devices have long been known in the art. Traditional prophylactic devices take the form of an elongated condom that is wrapped around the sheath of penis. While operable for catching semen and preventing the spread of sexually transmitted diseases, such devices cover up much of the penis and its sensitive zones. In other words, because a traditional condom covers most of the penis, the resulting pleasure of a male user is largely decreased.

Thus, a continuing need exists for a prophylactic device that is operable for catching semen and preventing the spread of sexually transmitted diseases, while not covering the sensitive tissue of the penis.

SUMMARY OF INVENTION

This disclosure provides a penile implement for adhering to the glans of a penis. The penile implement that can be implemented as both a catheter device and a prophylactic device. The penile implement is formed of a top film (e.g., polyurethane film), with a bottom film (e.g., polyurethane film) that is adhered (e.g., RF welded) to the top film such that a reservoir exists between the films. An adhesive layer formed on the bottom film and a bottom release layer covers the adhesive layer. Further, a hole is formed in the bottom film. Thus, during use, a user may remove the bottom release layer and adhere the bottom film with a user's penis such that bodily fluids secreted from the user's penis pass through the hole and into the reservoir formed between the top film and bottom film.

In another aspect, a top release layer covers at least a portion of the top film.

In yet another aspect, the penile implement is shaped to include one or more lateral projections.

Additionally, the penile implement is shaped to include an extended tail extending away from the hole, with the extended tail terminating with a pair of tail lateral projections.

In yet another aspect, a pair of meatus lateral projections project laterally from the hole.

Further, a pair of glans lateral projections formed proximate the meatus lateral projections.

In yet another aspect, all peripheral edges of the top film and bottom film are adhered to one another such that sole access to the reservoir is through the hole in the bottom film, thereby creating a prophylactic device.

In yet another aspect, an outlet is connected with the top film such that access to the reservoir is provided through the hole in the bottom film, with an exit to the reservoir being provided by the outlet, thereby creating a catheter device.

In another aspect, the outlet is a flanged tubing.

In yet another aspect, the top film and bottom film are each formed in a u-shape.

Finally, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 6A is an illustration depicting a top-side view of a prophylactic device according to various embodiments;

FIG. 6B is an illustration depicting a bottom-side view of the prophylactic device as depicted in FIG. 6A:

FIG. 7E is an illustration of a final cut layout of a prophylactic device according to various embodiments;

FIG. 7F is an illustration of an RF welding layout of a prophylactic device according to various embodiments;

FIG. 9C is an illustration depicting a pre-cut blank with a paper backing according to various embodiments; and FIG. 9D is an illustration depicting a pre-cut blank with a polyurethane top film.

DETAILED DESCRIPTION

The present invention relates to a penile implement and, in various embodiments, to a prophylactic device having a substrate (e.g., two tiered) for adhering to the glans of a penis. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

Figure 1:
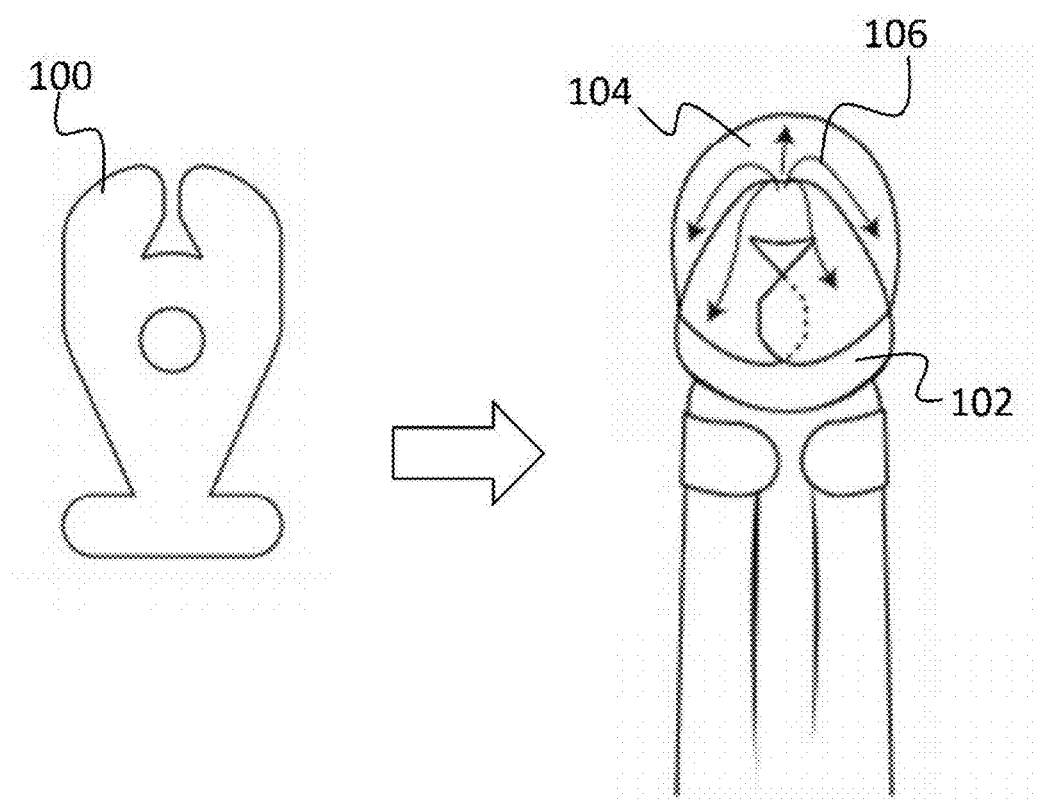
FIG. 1 is an illustration of a prophylactic device according to various embodiments, depicting the device as being adhered to the glans of a penis.

As noted above and as shown in FIG. 1, this disclosure provides a penile implement 100, such as a prophylactic device, for adhering to the glans of a penis 102. This creates a reservoir 104 (i.e., pouch) for trapping bodily fluids 106 (such as semen and urine) during sexual intercourse or urination. Primarily, the penile implement is to be used a condom (i.e., prophylactic device) but it may also be implemented as a catheter device. Regardless of the implementation, the penile implement 100 is formed to adhere with the glans of a penis 102 and includes a reservoir 104.

Figure 2:
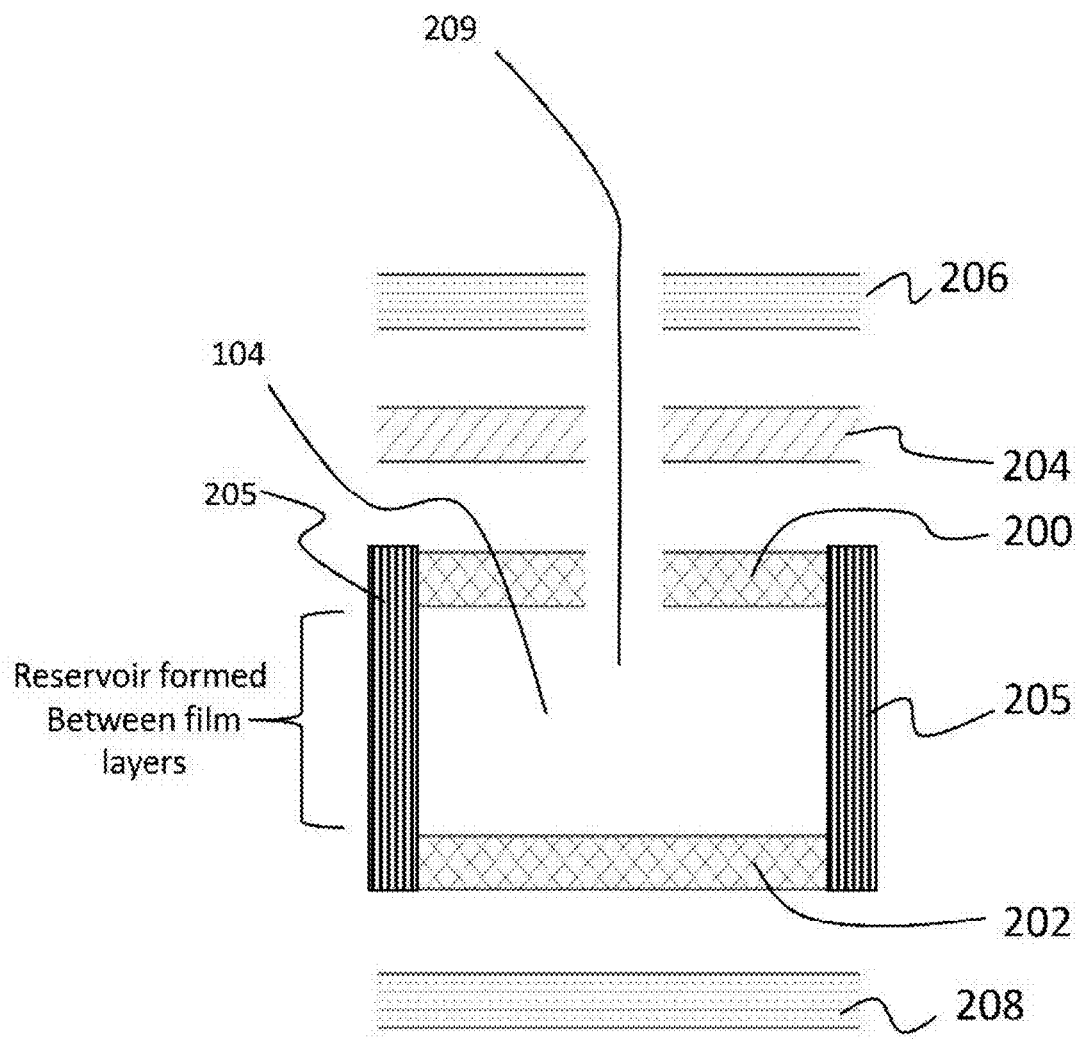
FIG. 2 is an illustration depicting components of the prophylactic device according to various embodiments.

The reservoir 104 can be formed using any suitable method or technique. As a non-limiting example and as shown in FIG. 2, the two layers of film can be connected with one another to form the reservoir 104 therebetween. The film is any suitable film that is suitable for use as a prophylactic device, a non-limiting example of which includes a polyurethane film. For example, a first bottom film 200 (e.g., polyurethane film) is adhered to a second top film 202 (e.g., polyurethane film). The films 200 and 202 are adhered to one another using any suitable connection method or technique, non-limiting examples of which include RF welding (also known as High Frequency (HF) welding or Dielectric welding) or plastic welding. In this example, edges of the bottom film 200 and top film 202 are welded 205 together, sealing only the edges of the films to create the reservoir 104 between the layers of film 200 and 202. RF welding is a method of joining thin sheets of polar thermoplastic material together. Further, a hole 209 can be formed in one of the films, such that once the bottom film 200 is adhered to the top film 202, the reservoir 104 is formed between the two layers of film 200 and 202 to capture semen or other bodily fluids that is introduced via the hole 209.

To adhere the films 200 and 202 to the penis and protect the films 200 and 202 during application, additional layers or components are added to the films 200 and 202. For example, the bottom film 200 includes an adhesive layer 204 that is used to adhere the prophylactic device to the penis. The adhesive layer 201 is, for example, a medical grade adhesive that is applied to the bottom film 200. To protect the adhesive layer 204 prior to application, a bottom release layer 206 (e.g., release paper or film) is positioned over the adhesive layer 204. Conversely, the top film 202 optionally includes a top release layer 208 (e.g., release paper or film) to protect the top film 202 from damage due to storage or puncture prior to application and provide stability during application. Further, the hole 209 can be formed using any suitable technique or method. As a non-limiting example, the stack of bottom film 200, adhesive layer 204, and bottom release layer 206 can be punched or die cut to form the hole 209 through all three layers (200, 204, and 206) which provides access to the reservoir 104 when the bottom film 200 is adhered to the top film 202.

There are several different penile implements that can be implemented and formed based on the concept as described above of adhering film (e.g., dual-layer film) to a penis for catching semen or other fluids in a reservoir (e.g., formed between the two layers of film). Various non-limiting examples are described, in further detail below.

(1) One Piece Cap

Figure 3:
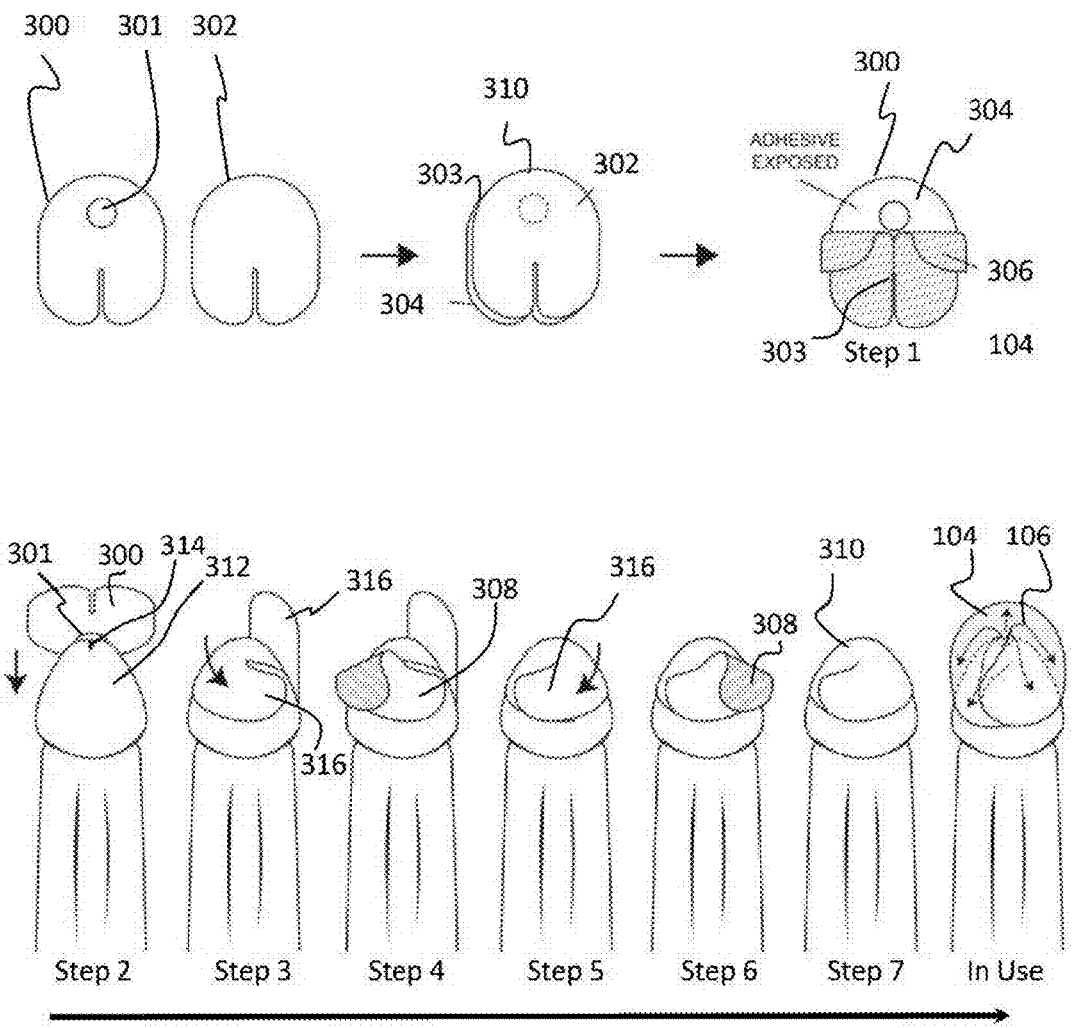
FIG. 3 is an illustration depicting a prophylactic device according to various embodiments, depicting the device as being adhered to the glans of a penis.

As shown in FIG. 3, one example embodiment is a prophylactic device. In this example, the prophylactic device is directed to a one piece cap 310 formed according to the method as described above regarding FIG. 2. FIG. 3 depicts the one piece cap 310 along with a process for applying the one piece cap 310. In this example, the bottom film 300 includes a hole 301 formed therethrough, while the top film 302 includes no such hole. Thus, the hole 301 provides an opening to the reservoir formed between the bottom film 300 and top film 302. As described in further detail below, the one piece cap 310 fits over the head of the penis and has an opening over the meatus (the hole) allowing the bodily fluids to enter the pouch and be trapped in its reservoir.

In this example, each of the films 300 and 302 are formed as identical U-shaped polyurethane films that are RF welded together around their peripheral edges 303 to create a reservoir to capture semen or fluids. The top film 302 has no adhesive while the bottom film 300 has an adhesive 304 (e.g., adhesive layer). All of the peripheral edges are sealed (e.g., RF welded) and the hole 301 is cut (e.g., prior to RF welding) in the bottom film 300 which will cover the meatus (i.e., the opening of the urethra).

The release layers (e.g., release paper) are optionally scored 303 in the middle, much like a Band-Aid®, and is attached to both the top and bottom films. Top and bottom release layers 306 and 308 can be made of the same or different materials. The bottom release layer 306 serves to cover and protect the adhesive layer 304 that covers the bottom film 300. The top release layer 308 serves to provide stability to both films 300 and 302 during application.

As shown in Step 1, when the user is ready for sex or otherwise ready to apply the prophylactic device (e.g., one piece cap 310), the bottom release layer 306 is split and peeled off exposing the adhesive layer 304 on the bottom film 300. As shown in Step 2, the bottom film 300 is then lowered and placed on the glans 312 (head for the penis). The hole 301 is aligned with the meatus (pee hole) 314 in the condom, ensuring that ejaculated semen will flow into the reservoir.

As shown in Steps 3 through 7, the bottom film is adhered to the glans 312 starting with the back of the glans and moving forward. The edges 316 (formed by the u-shape) are crisscrossed around the head of the penis overlapping on the long side of the glans. As each edge 316 is laid into position, its corresponding top release layer 308 is removed. Thus, in this example and as shown in Step 7, the prophylactic device (i.e., one piece cap 310) is now properly in place. When the user has sex and ejaculates, the semen (or bodily fluids 106) goes thru the hole into the condom and is captured in the device reservoir 104.

(2) Two Piece

Figure 4:
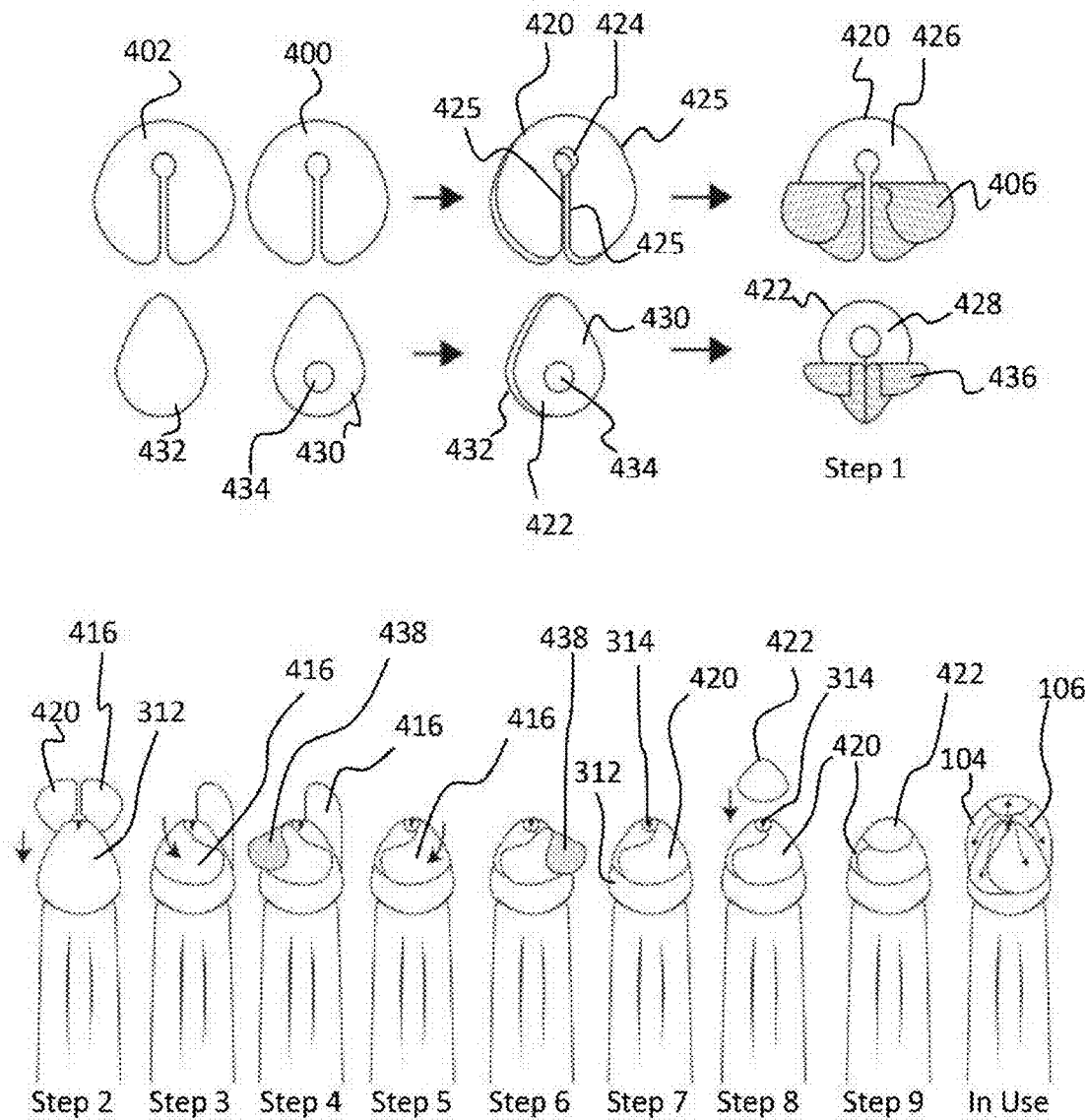
FIG. 4 is an illustration depicting a prophylactic device according to various embodiments, depicting the device as being adhered to the glans of a penis.

As shown in FIG. 4, one example embodiment of the prophylactic device is directed to a two piece design, having a first part 420 and a second part 422. The two piece design is formed and performs much the same as the one piece cap (described above) in that the first part 420 includes two identical u-shaped pieces of film (e.g., polyurethane) that are RF welded at the edges. Like the one piece cap, the bottom and top films 400 and 402 have top and bottom release layers (e.g., release paper) and the bottom film 400 also includes a medical grade adhesive that is covered by the release layer.

The difference is that the first part 420 of the two piece design wraps around the meatus (pee hole) leaving it exposed for urination. The circular edges 424 around the meatus are not RF welded and remain unattached, while all other peripheral edges 425 (aside from the circular edges 424 around the meatus) are RF welded (or otherwise attached) to form a cavity (reservoir) between the bottom and top films 400 and 402. Access to the cavity or reservoir is achieved by the gap between the circular edges 424 of each of the bottom and top films 400 and 402.

As noted above, the two piece design also includes a second part 422. The second part 422 is also formed of bottom and top films 430 and 432 that are adhered to one another (e.g., RF welding) and, in of itself, is formed very similar to the one piece cap as described above (including the hole 434 in the bottom film 430 that provides access to the reservoir between the bottom and top films 430 and 432 (which are, for example, RF welded together)). Although the second part 422 does not include the u-shaped design of the one piece cap, it does include the adhesive layer and release layers 436.

As shown in Step 1, the release layers 406 and 436 are removed from the first and second parts 420 and 422 to expose the relevant adhesive layers 426 and 428. With the adhesive layer 426 exposed, the first part 420 is adhered to the glans 312 of the penis (as shown in Steps 2 through 6), starting with the back of the glans 312 and moving forward. The edges 416 (formed by the u-shape) are crisscrossed around the head of the penis overlapping on the long side of the glans 312. As each edge 416 is laid into position, its corresponding top release layer 438 is removed. As shown in Step 8 and to be contrasted with the one piece cap described above, the first part 420 is adhered to the glans 312 such that it wraps around the glans 312 while leaving the meatus 314 uncovered. As shown in Step 8, when ready for intercourse or otherwise ready for bodily fluid release, a user must adhere the second part 422 to the first part 420 such that the hole 434 on the bottom film 430 is aligned with the meatus 314 (and covers the meatus as shown in Step 9).

In this aspect, the user can put on the first part 420 at any appropriate time, including hours or even days before intercourse. When intercourse is ready to occur, the meatus opening is simply covered over with the second part 422, which seals off the hole 434 and forms an air tight reservoir into which the semen may be captured. In other words and as shown in use, semen or bodily fluids 106 can be captured in one or both reservoirs 104 as formed in each of the first and second parts 420 and 422.

(3) Anchor

Figure 5A:
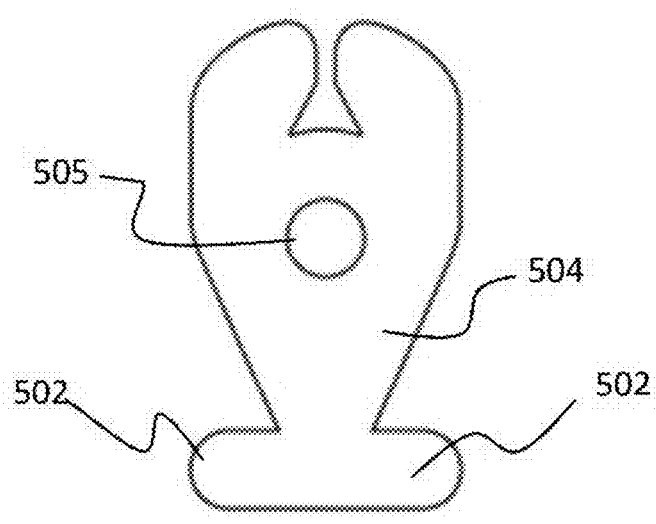
FIG. 5A is an illustration depicting a prophylactic device according to various embodiments.
Figure 5B:
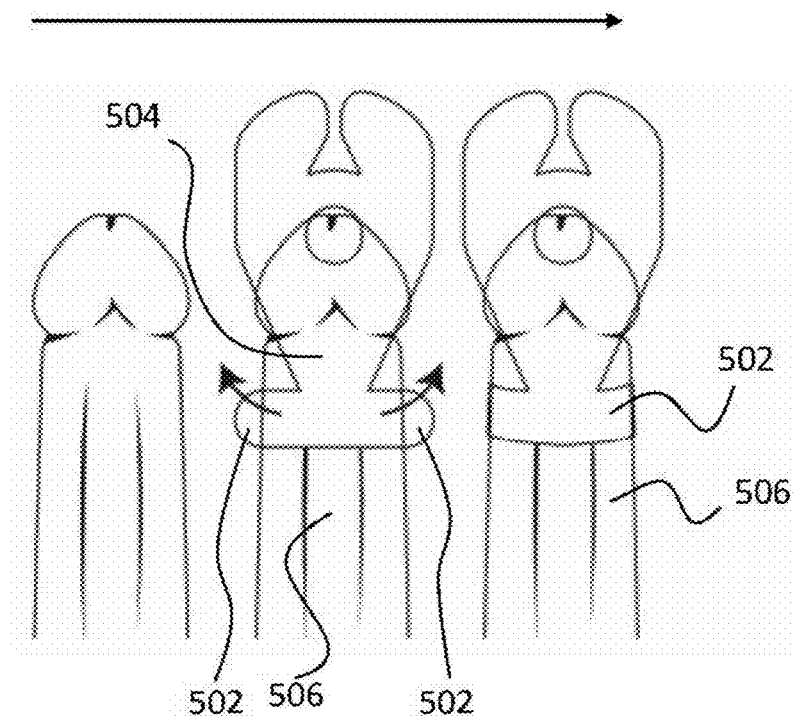
FIG. 5B is an illustration depicting the prophylactic device of FIG. 5A as being adhered to the glans of a penis.
Figure 5C:
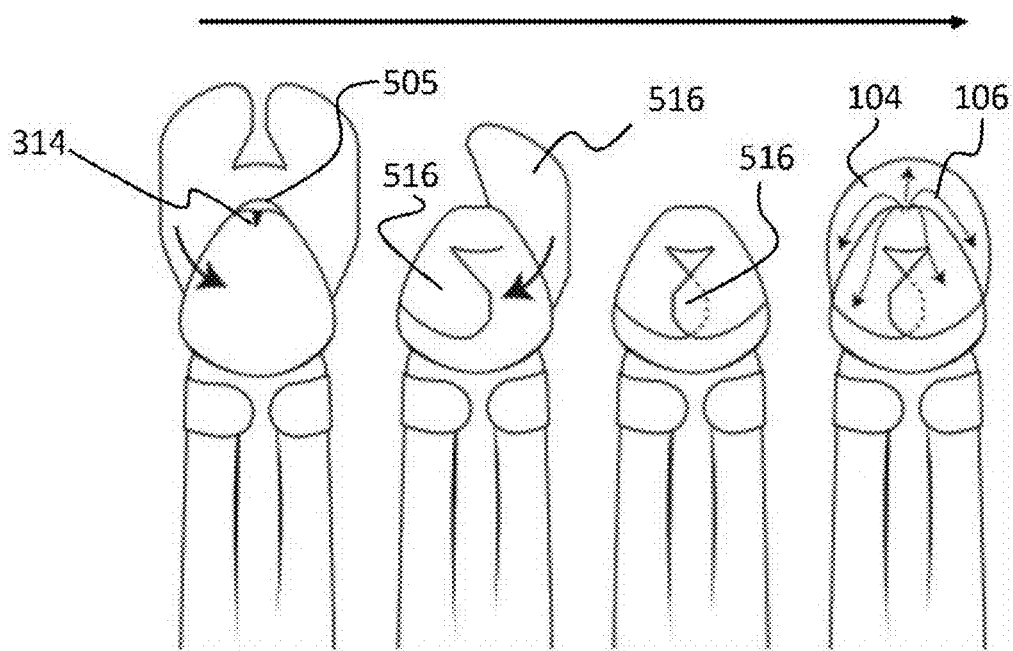
FIG. 5C is an illustration depicting the prophylactic device of FIG. 5A as being adhered to the glans of a penis.

As shown in FIGS. 5A through 5C, one example embodiment of the prophylactic device is directed to an anchor design 500 having one or more lateral projections 502. While the anchor design 500 is formed to have the same hole 505 and components as those described above with respect to FIG. 2 and the one piece cap shape, the anchor design 500 is simply shaped differently because the shape of the head of the penis differs from man to man. Most men have a shape similar to a fireman's hat (i.e., long on one side and short on the other). The adhesive film works very well on the long side, because the coronal ridge protects it from friction and abrasion during sex. However, on the short side of the glans, there is less of a ridge for protection. Under intensive oral, vaginal and/or anal fiction, the condom can start to peel off on the back side and ultimately fail, allowing semen to escape.

To prevent this from happening, the anchor design 500 extends a tail 504 along with one or more lateral polyurethane adhesive strips (i.e., lateral projections 502) down the back side of the penis. The feature of the extended tail 504 and lateral projections 502 can be added to both the one piece cap and two piece designs as described above.

As shown in the bottom view of FIG. 5B, the extended tail 504 allows the lateral projections 502 to extend down to the shaft 506 of the penis and wrap around the shaft 506 to provide for a more secure connection. Once adhered to the shaft 506, the remainder of the prophylactic device can be attached with the head of the penis (as shown in FIG. 5C) such that the hole 505 is aligned with the meatus 314 (similar to the one piece cap design). If the anchor design 500 includes edges 516 (formed by the u-shape), the edges 516 are crisscrossed around the head of the penis overlapping on the long side of the glans. As each edge 516 is laid into position, its corresponding top release layer is removed. Once affixed, a user can release bodily fluid 106 into the reservoir 104 as formed between the bottom and top films.

Additional anchor designs are depicted in FIGS. 6A through 8 and described in further detail below. It should be noted that all of the designs and shapes as described herein can be formed in any suitable method or technique that allows for adhesion to a glans and capture of bodily fluid in a reservoir. However, in various embodiments, the designs, including the anchor design of FIG. 5 and additional anchor designs as depicted in FIGS. 6A through 8, are formed according to the process as described above with respect to FIG. 2, including the top and bottom film layers, adhesive layer, and top and bottom release layers (or any combination thereof) as shown in FIGS. 2-4, which are removed during appropriate and similar application times as shown in FIGS. 3 and 4.

For example, another anchor design is illustrated in FIGS. 6A and 6B, which depict top and bottom sides (the bottom side being the side facing the meatus and glans), respectively, of the prophylactic device 600. As shown in the top side of FIG. 6A, the top release layer 602 can be removed to expose the top film 604. Similarly and as shown in the bottom side view of FIG. 6B, the bottom release layer 606 can be removed to expose the adhesive layer 608. Notably, the prophylactic device 600 as depicted in FIGS. 6A and 6B includes an extended tail 610 and multiple lateral projections, all of which are formed strategically to further enhance the adhesion of the device 600 to the penis. For example, straddling the hole 612 in the bottom film are a pair of meatus lateral projections 614. The meatus lateral projections 614 operate to securely affix and align the hole 612 with the meatus. Proximate the meatus lateral projections 614 are a pair of glans lateral projections 616. The glans lateral projections 616 serve to securely affix the device 600 with the glans of the penis (e.g., dorsal side of the glans) while preventing the hole 612 from sliding toward the ventral side of the penis. Further, the extend tail 610 terminates in a pair of tail lateral projections 618. The tail lateral projections 618 serve to secure the device 600 with the shaft of the penis while anchoring the device 600 and preventing the hole 612 from sliding toward the dorsal side of the penis.

Figure 6C:
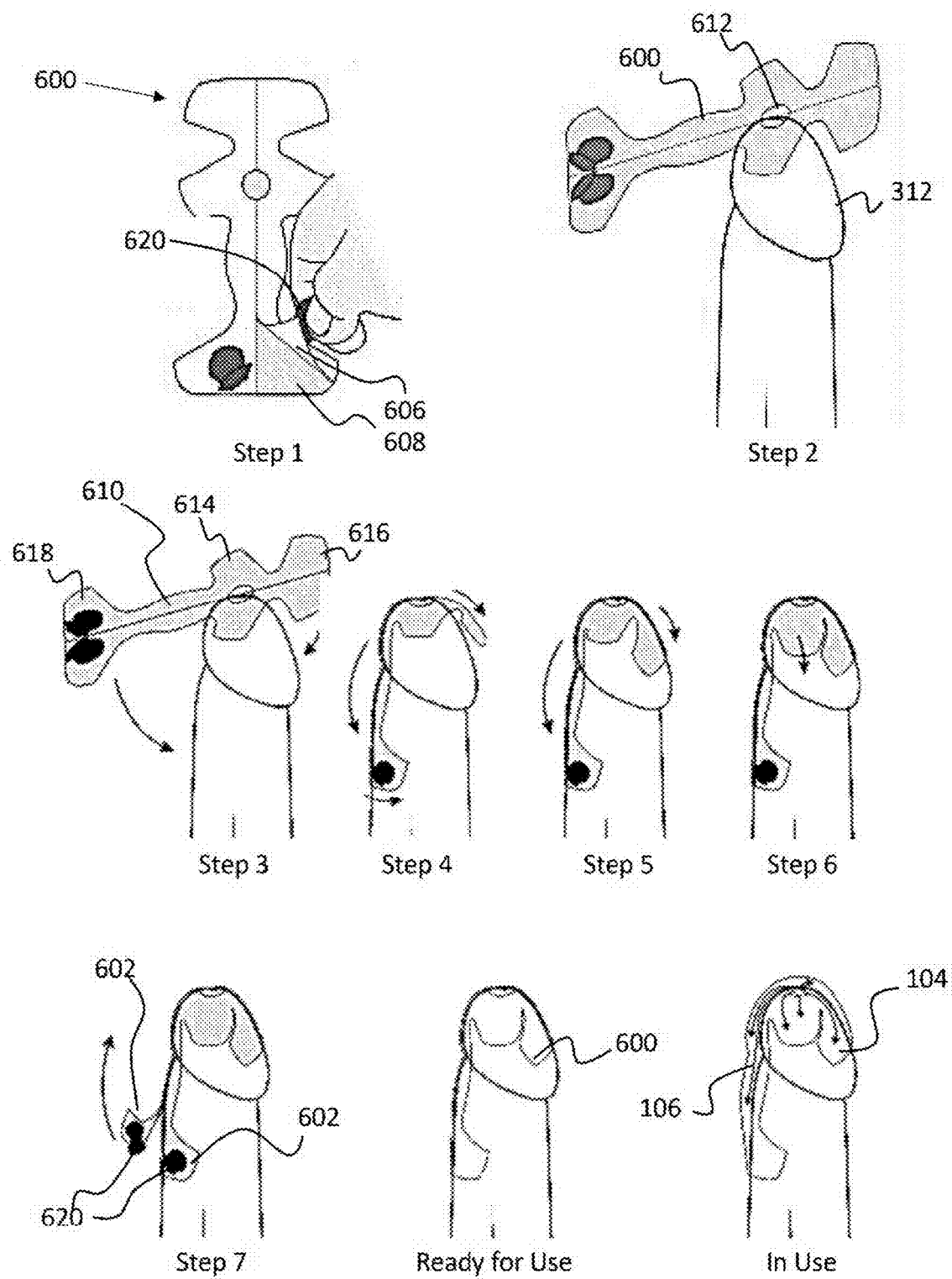
FIG. 6C is an illustration depicting the prophylactic device of FIGS. 6A and 6B as being adhered to the glans of a penis.

One or more pull tabs 620 can also optionally be adhered to the top and/or bottom release layers 602 and 606. The pull tabs 620 allow a user to easily remove the relevant release layer 602 and 606 during the appropriate time during application. This aspect is further depicted in FIG. 6C. For example and as shown in Step 1, a user would use the pull tab 620 (if included) to lift and remove the bottom release layer 606 to expose the adhesive layer 608 (adhesive surface). Once the penis is erect and as shown in Step 2, the adhesive layer 608 is then placed on the glans 312, aligning the hole 612 of the device 600 with the meatus (i.e., pee hole). As shown in Steps 3 through 6, once the holes (i.e., hole 612 and meatus) are aligned, the bottom (i.e., tail 610 and tail lateral projections 618) of the device 600 is applied to the shaft and the top (i.e., meatus lateral projections 614 and glans lateral projections 616) is applied to the head or glans of the penis. Once applied and as shown in Step 8, a user can remove both of the top release layers 602 (i.e., both halves). Note that each of the top and bottom release layers can be a single sheet or cut such that it is more than one piece. For example, and as shown in FIGS. 6A and 6B, the top and bottom release layers 602 and 606 can be cut in half (e.g., die cut) such that a user only removes one half of each release layer at a time (which enhances the ease of application). Also as noted, the top release layer 602 optionally includes the pull tabs 620 to assist the user in removing each half of the top release layer 602. After being applied the device 600 is then ready for use. Thus, in use, bodily fluids 106 are captured in the reservoir 104.

Figures 7A, 7B:
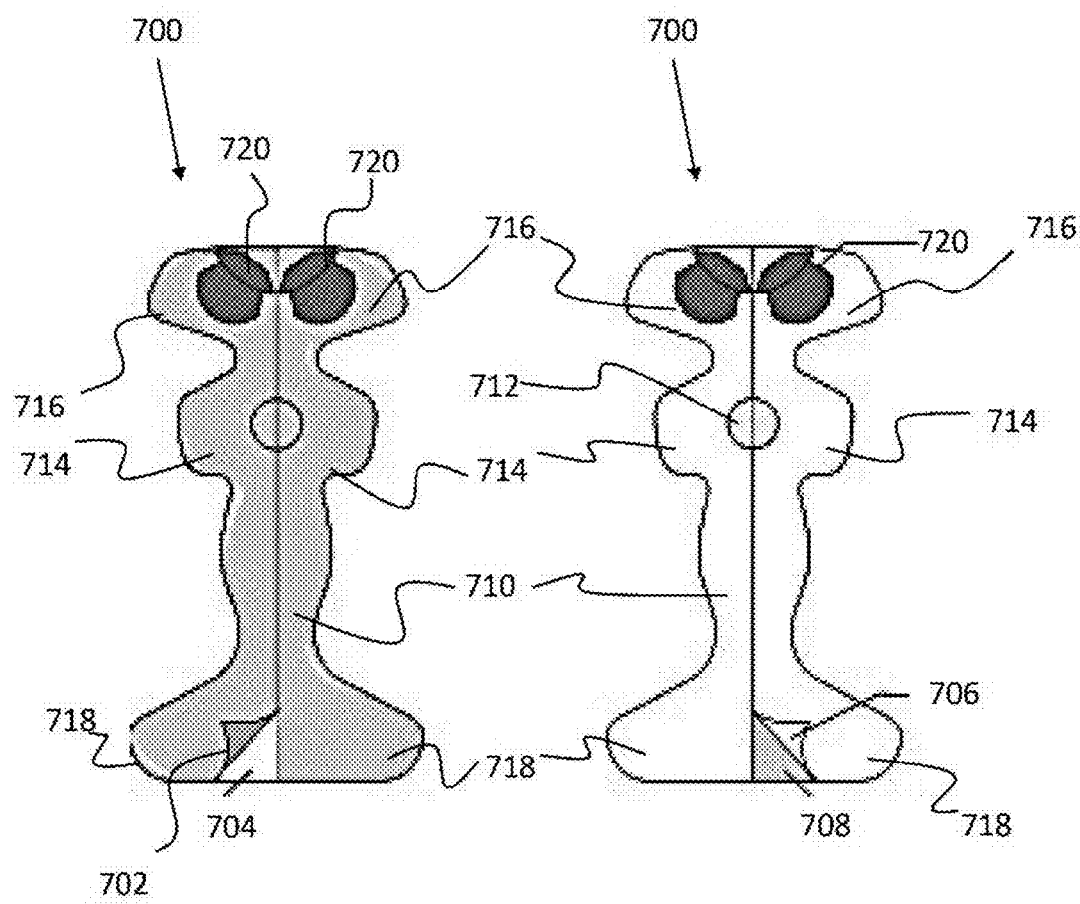
FIG. 7A is an illustration depicting a top-side view of a prophylactic device according to various embodiments.
FIG. 7B is an illustration depicting a bottom-side view of the prophylactic device as depicted in FIG. 7A.

Yet another anchor design is illustrated in FIGS. 7A and 7B, which depict to and bottom sides (the bottom side being the side facing the meatus and glans), respectively, of the prophylactic device 700. As was the case above and as shown in the top side of FIG. 7A, the top release layer 702 can be removed to expose the top film 704. Similarly and as shown in the bottom side view of FIG. 7B, the bottom release layer 706 can be removed to expose the adhesive layer 708. Also as was the case above, the prophylactic device 700 as depicted in FIGS. 7A and 7B includes an extended tail 710 and multiple lateral projections, all of which are formed strategically to further enhance the adhesion of the device 700 to the penis. For example, straddling the hole 712 in the bottom film are a pair of meatus lateral projections 714. The meatus lateral projections 714 operate to securely affix and align the hole 712 with the meatus. Proximate the meatus lateral projections 714 are a pair of glans lateral projections 716. The glans lateral projections 716 serve to securely affix the device 700 with the glans of the penis (e.g., dorsal side of the glans) while preventing the hole 712 from sliding toward the ventral side of the penis. Further, the extend tail 710 terminates in a pair of tail lateral projections 718. The tail lateral projections 718 serve to secure the device 700 with the shaft of the penis while anchoring the device 700 and preventing the hole 712 from sliding toward the dorsal side of the penis. One or more pull tabs 720 can also optionally be adhered (at any desired location) to the top and bottom release layers 702 and 705.

While very similar to the device 600 shown in FIGS. 6A and 6B, the device 700 of FIGS. 7A and 7B includes the pull tabs 720 at the top (i.e., on the glans lateral projections 716) as opposed to the tail lateral projections 618 of the device 600 described above. Adhering the pull tabs 720 at the top provides for a more natural application and enables to user to selectively attach the top of the device 700 to the penis and progressively remove the bottom release layer 706. Further, the device 700 of FIGS. 7A and 7B includes lateral projections (714, 716 and 718) that are all shorter than the lateral projections (614, 616, and 618) of the device 600 of FIGS. 6A and 6B. The shorter lateral projections allow for easier application as there is less material that needs to be worked with during application.

Figure 7C:
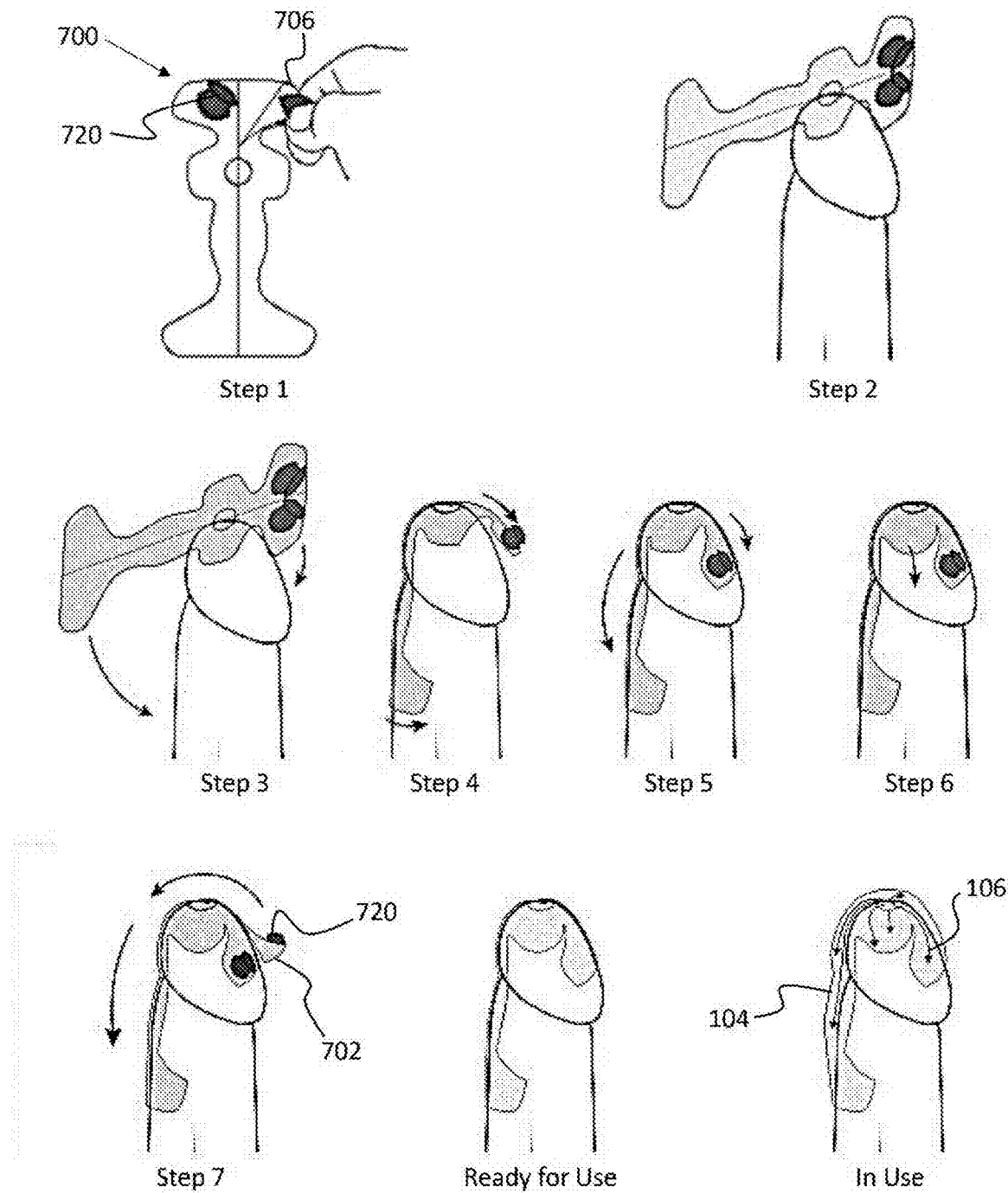
FIG. 7C is an illustration depicting the prophylactic device of FIGS. 7A and 7B as being adhered to the glans of a penis.

An example application process is depicted as Steps 1 through 7 in FIG. 7C. The device 700 of FIG. 7C can be applied in the same manner as that of the device 600 of FIG. 6C, with the distinction being the location and direction at which the pull tabs 720 are used to remove the relevant release layers 702 and 706. Similarly and during use, the reservoir 104 is filled with the bodily fluid 106, which expands and fill the reservoir 104.

Figure 7D:
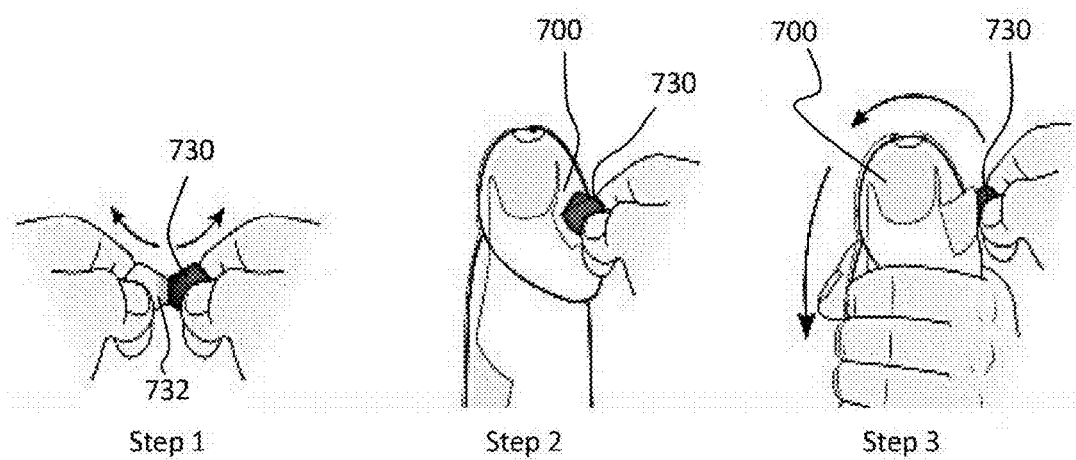
FIG. 7D is an illustration depicting a process of removing the prophylactic device according to various embodiments.
Figure 8:
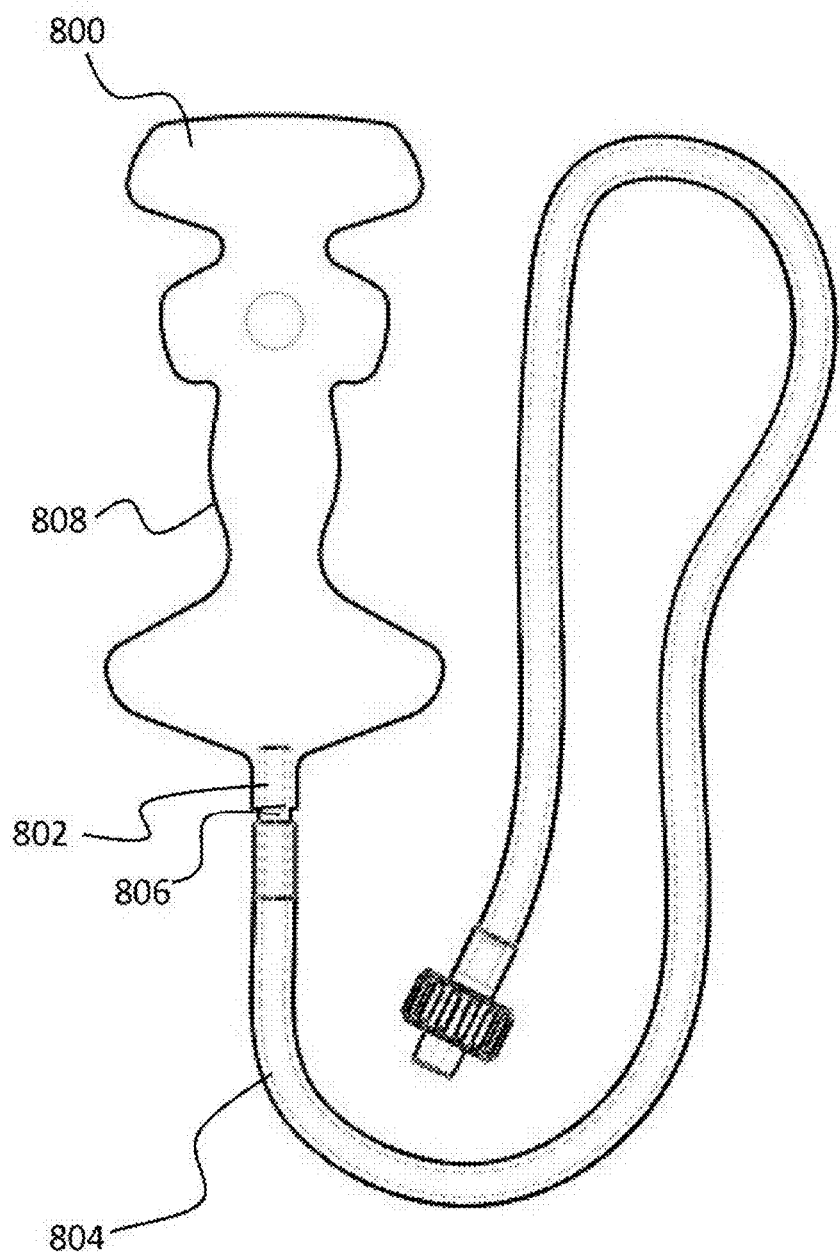
FIG. 8 is an illustration depicting a catheter device according to various embodiments.

After use, the penile implants (e.g., prophylactic devices and catheter device) as described herein can be removed and discarded. To assist in removal and as shown in FIG. 7D, loose pull tabs can be optionally included. As shown in Step 1 of FIG. 7D, the loose pull tabs 730 include a release liner 732 that can be removed to expose an adhesive surface on the loose pull tab 730. As shown in Step 2, the loose pull tab 730 can then be adhered to any edge of the penile implant (e.g., prophylactic device 700). As shown in Step 3, pulling on the now adhered loose pull tab 730 loosens the edge of the device 700 from the skin, allowing the user to slowly peel off the device, much like removing a Band-Aid®. It should be understood that the loose pull tabs 730 are not initially attached with the prophylactic device 700 and, importantly, can be used with any of the prophylactic devices or embodiments described herein.

Further, it should be understood that the penile implements as described herein, including but not limited to the one piece cap, two piece design, and various anchor designs, can be formed in any suitable dimension. For example, FIGS. 7E and 7F illustrate dimensions (in inches) of a final cut layout 740 and RF welding layout 742, respectively, of the prophylactic device 700 of FIG. 7.

(4) Catheter

As noted above and as shown in FIG. 8, the device as described herein can be implemented as a catheter device 800. The catheter device 800 can be formed using any suitable mechanism, technique, or method that allows the device 800 to adhere to a user's penis and receive urine in its cavity during urination. For example, the catheter device 800 includes the film layers, adhesive layer, and one more of the release layers as described above with respect to the various embodiments and as illustrated in FIG. 2.

The urine can be discharged from the cavity via an outlet 802 that can be connected with a discharge conduit 804 or tubing. The outlet 802 can be formed using any suitable method, technique or device for providing an outlet to a flexible container. As a non-limiting example, the outlet 802 is formed via a plastic pipe 806 that is adhered between (and protrudes from) each of the top and bottom films, with the edges 808 of said films being RF welded together.

Another example of a catheter device 900 is depicted in FIGS. 9A through 9D. As was the case above, the catheter device 900 can be formed using any suitable mechanism, technique, or method that allows the device 900 to adhere to a user's penis and receive urine in its cavity during urination. For example, the catheter device 900 includes the film layers, adhesive layer, and one more of the release layers as described above with respect to the various embodiments and as illustrated in FIG. 2. To be contrasted with the catheter device described above, the device 900 as shown in FIGS. 9A and 9B includes an outlet that is a flanged tubing 902 that is pre-adhered (e.g., RF welded) to the top film such that it is aligned with the hole 901 and, subsequently, with the meatus of the penis when applied to a user. This assists in directing the urine out of the catheter device 900 (via the flanged tubing 902) and through the relevant tubing into a catch bag or other container. As noted in the shape, the catheter device 900 may be formed to include and extended tail 904 and one or more lateral projections, non-limiting examples of which include glans lateral projections 906 and meatus lateral projections 908 (that straddle the hole 901).

Additionally, the catheter device 900 is shown as having extended cars 910. The extended ears 910 are extensions of the top release layer (or bottom release layer) that has no film or adhesive layers attached thereto. In other words, the extended ears 910 are, for example, paper layers that extend beyond the top film layer (or bottom film layer) that act as tabs to allow a user to easily remove the device 900. It should be noted that the extended ears 910 can be applied, as desired, to any of the penile implements as described throughout this disclosure.

Figure 9A:
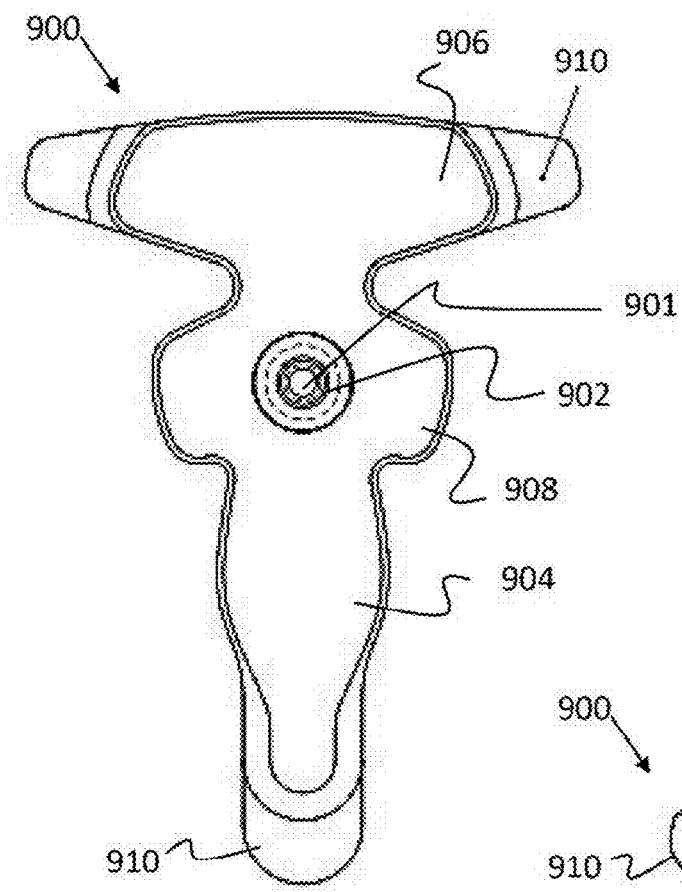
FIG. 9A is an illustration depicting a catheter device according to various embodiments.
Figure 9B:
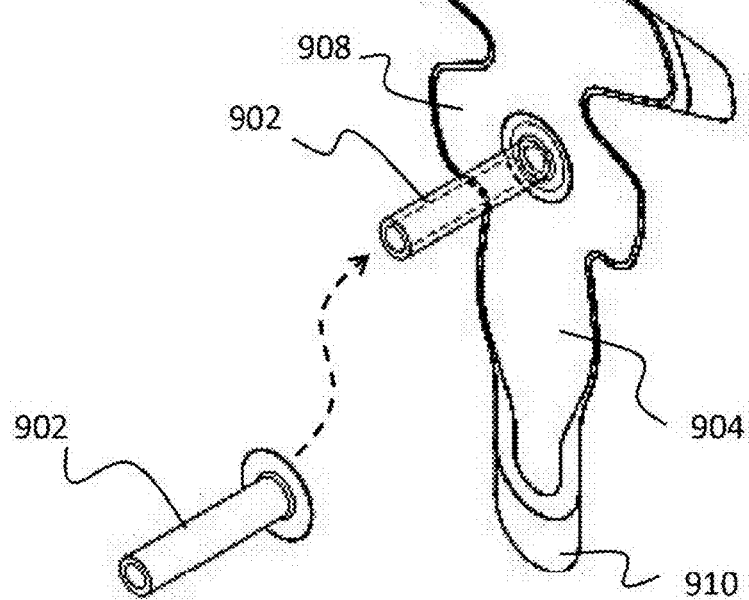
FIG. 9B is an illustration depicting the catheter device of FIG. 9A.

The catheter device 900 as shown in FIGS. 9A and 9B can be formed in any suitable manner such that it includes the multiple film layers and a flanged tubing that protrudes from the top film. For example, FIG. 9C depicts a pre-cut blank (inner blank) with a paper backing (i.e., bottom film with adhesive layer and bottom release layer) while FIG. 9D depicts a pre-cut blank (outer blank) with a polyurethane top film. A location of a final profile weld 912 (e.g. RF weld) is shown in FIG. 9C. Referring to the FIG. 9D, the flanged portions of the flanged tubing (shown in FIG. 9B as element 902) is pre-adhered (e.g., RF welded) to the outer blank around the tubing hole 914. Thereafter, the two blanks (i.e., the inner blank of FIG. 9C and outer blank of FIG. 9D) are adhered to one another along, for example, the final profile weld 912. Once the two blanks are adhered to one another, the catheter device can be completed, for example, by cutting (die cutting, stamping, etc.) the films and layers along the final cut profile 916.

Given the description above, it should be understood by those skilled in the art that the penile implement as described throughout this disclosure can be used as both a prophylactic device and a catheter device, or any other suitable implementation. As such, it is generically referred to as a penile implement, which in one implementation is a prophylactic device while in another implementation is a catheter device. Further, it should be noted that the steps as described and depicted are provided for illustrative purposes only and that the invention is not intended to be limited to those particular steps or order of steps.

It should also be noted that the specific shapes as described and illustrated are provided as non-limiting examples of suitable shapes and that the invention is not intended to be limited thereto. Additionally, it should be understood that although various example embodiments are disclosed, the features of any one embodiment can be applied to or interchanged as desired in any other embodiment. Further, the invention is described as having two films that are RF welded together. RF welding is provided as a non-limiting example of attaching separate components for forming, the reservoir; however, notably, the invention is not intended to be limited thereto as the reservoir can be formed using any suitable method or technique, non-limiting examples of which include gluing the two films together, molding a film (or films) into a continuous shape that includes such a reservoir, etc. Additionally, although the term "film" is used throughout, it should be understood that although a polyurethane film is provided as a suitable example embodiment, the invention is not intended to be limited thereto as any suitably flexible and thin, sheet like material may be used, other examples of which include rubber, sheep skin, etc.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A penile implement comprising:
   a top film;
   a bottom film adhered to the top film such that a reservoir exists between the top film and bottom film, wherein each of the top film and bottom film are distinct films that are welded, or glued to one another;
   an adhesive layer formed on the bottom film;
   a bottom release layer covering at least a portion of the adhesive layer; and
   wherein a hole is formed in the bottom film, whereby during use, a user may remove the bottom release layer and adhere the bottom film with a user's penis such that bodily fluids secreted from the user's penis pass through the hole and into the reservoir formed between the top film and bottom film.

2. The penile implement as, set forth in claim 1, wherein each of the top film and bottom film are polyurethane films that are radio frequency welded to one another.

3. The penile implement as set forth in claim 2, further comprising a top release layer covering at least a portion of the top film.

4. The penile implement as set forth in claim 3, wherein the penile implement is shaped to include one or more lateral projections.

5. The penile implement as set forth in claim 3, wherein the top film and bottom film are each formed in a u-shape.

6. The penile implement as set forth in claim 1, wherein the penile implement is shaped to include one or more lateral projections.

7. The penile implement as set forth in claim 1, wherein all peripheral edges of the top film and bottom film are adhered to one another such that sole access to the reservoir is through the hole in the bottom film, thereby creating a prophylactic device.

8. A penile implement, comprising:
a top film;
a bottom film adhered to the top film such that a reservoir exists between the top film and bottom film;
an adhesive layer formed on the bottom film;
a bottom release layer covering at least a portion of the adhesive layer;
wherein a hole is formed in the bottom film, whereby during use, a user may remove the bottom release layer and adhere the bottom film with a user's penis such that bodily fluids secreted from the user's penis pass through the hole and into the reservoir formed between the top film and bottom film;
wherein each of the top film and bottom film are polyurethane films that are radio frequency welded to one another;
further comprising a top release layer covering at least a portion of the top film;
wherein the penile implement is shaped to include one or more lateral projections; and
wherein the penile implement is shaped to include an extended tail extending away from the hole, with the extended tail terminating with a pair of tail lateral projections.

9. The penile implement as set forth in claim 8, further comprising a pair of meatus lateral projections projecting laterally from the hole.

10. The penile implement as set forth in claim 9, further comprising a pair of glans lateral projections formed proximate the meatus lateral projections.

11. The penile implement as set forth in claim 10, wherein an outlet is connected with the top film such that access to the reservoir is provided through the hole in the bottom film, with an exit to the reservoir being provided by the outlet, thereby creating a catheter device.

12. The penile implement as set forth in claim 11, wherein the outlet is a flanged tubing.

13. The penile implement as set forth in claim 10, wherein all peripheral edges of the top film and bottom film are adhered to one another such that sole access to the reservoir is through the hole in the bottom film, thereby creating a prophylactic device.

14. A penile implement, comprising:
a top film;
a bottom film adhered to the top film such that a reservoir exists between the top film and bottom film;
an adhesive layer formed on the bottom film;
a bottom release layer covering at least a portion of the adhesive layer;
wherein a hole is formed in the bottom film, whereby during use, a user may remove the bottom release layer and adhere the bottom film with a user's penis such that bodily fluids secreted from the user's penis pass through the hole and into the reservoir formed between the top film and bottom film; and wherein the penile implement is shaped to include an extended tail extending away from the hole, with the extended tail terminating with a pair of tail lateral projections.

15. A penile implement, comprising:
a top film;
a bottom film adhered to the top film such that a reservoir exists between the top film and bottom film;
an adhesive layer formed on the bottom film;
a bottom, release layer covering at least a portion of the adhesive luer;
wherein a hole is formed in the bottom film, whereby during use, a user may remove the bottom release layer and adhere the bottom film with a user's penis such that bodily fluids secreted from the user's penis pass through the hole and into the reservoir formed between the top film and bottom film; and
further comprising a pair of meatus lateral projections projecting laterally from the hole.

16. A penile implement, comprising:
a top film;
a bottom film adhered to the top film such that a reservoir exists between the top film and bottom film;
an adhesive layer formed on the bottom film;
a bottom release layer covering at least a portion of the adhesive layer;
wherein a hole is formed in the bottom film, whereby during use, a user may remove the bottom release layer and adhere the bottom film with a user's penis such that bodily fluids secreted from the user's penis pass through the bole and into the reservoir formed between the top, film and bottom film; and
further comprising a pair of meatus lateral projections projecting laterally from the hole and a pair of glans lateral projections formed proximate the meatus lateral projections.

17. A penile implement, comprising:
a top film;
a bottom film adhered to the top film such that a reservoir exists between the top film and bottom film;
an adhesive layer formed on the bottom film;
a bottom release layer covering at least a portion of the adhesive layer;
wherein a hole is formed in the bottom film, whereby during use, a user may remove the bottom release layer and adhere the bottom film with a user's penis such that bodily fluids secreted from the user's penis pass through the hole and into the reservoir formed between the top film and bottom film; and
wherein an outlet is connected with the top film such that access to the reservoir is provided through the hole in the bottom film, with an exit to the reservoir being provided by the outlet, thereby creating a catheter device.

18. A penile implement, comprising:
a top film;
a bottom film adhered to the top film such that a reservoir exists between the top film and bottom film;
an adhesive layer formed on the bottom film;
a bottom release layer covering at least a portion of the adhesive layer;
wherein a hole is formed in the bottom film, whereby during case, a user may remove the bottom release layer and adhere the bottom film with a user's penis such that bodily fluids secreted from the user's penis pass through the hole and into the reservoir formed between the top film and bottom film; and wherein a flanged tubing is connected with the top film such that access to the reservoir s provided through the hole in the bottom film, with an exit to the reservoir being provided by the flanged tubing such that flanged tubing serves as an outlet, thereby creating a catheter device.

* * * * *